United States Patent [19] [11] 3,939,285
Garrett, Sr. et al. [45] Feb. 17, 1976

[54] METHOD OF MAKING AGGLOMERATES COMPRISED OF PARTICLES FOR CARRYING LIQUID

[75] Inventors: Charles B. Garrett, Sr.; Roger L. Garrett, both of Alexandria; Alan B. Rubin, Fairfax, all of Va.

[73] Assignee: Adams Laboratories, Inc., Alexandria, Va.

[22] Filed: Nov. 6, 1973

[21] Appl. No.: 413,214

[52] U.S. Cl. ................ 426/285; 426/310; 426/453; 426/335; 424/23; 424/26; 23/313 R; 23/313 AS
[51] Int. Cl.$^2$ ............................................ A23C 9/00
[58] Field of Search ........... 426/285, 453, 807, 147, 426/229, 371, 382, 437, 302, 310, 335; 23/313; 264/109, 117, 437; 424/16, 23, 24, 26, 31; 428/403; 252/410, 421, 424, 425, 427, 428, 477 R

[56] References Cited

UNITED STATES PATENTS 3,100,909 8/1963 Schapiro ............................ 426/285
3,311,477 3/1967 Segal .............................. 23/313 AS

FOREIGN PATENTS OR APPLICATIONS 560,490 7/1958 Canada

OTHER PUBLICATIONS

Condensed Chemical Dictionary –Hanley Van Nostrand Reinhold N.Y. 1971.

*Primary Examiner*—Norman Yudkoff
*Assistant Examiner*—Hiram H. Bernstein
*Attorney, Agent, or Firm*—Morris Liss

[57] ABSTRACT

A granular composition is comprised of primary carrier particles that are mixed with a liquid containing an active ingredient which saturates, by adsorption, the surface of each particle. A second carrier material is then mixed in so that secondary carrier particles adhere to the surface of each primary particle to form an agglomerate. The secondary carrier adsorbs additional liquid in the composition so that the composition may be handled as a granular mass.

10 Claims, 3 Drawing Figures

METHOD OF MAKING AGGLOMERATES COMPRISED OF PARTICLES FOR CARRYING LIQUID

SUMMARY AND BACKGROUND OF THE INVENTION

1. Field of the Invention:

The present invention relates to the formation of an agglomerate having a liquid adsorbed by carrier components, and more particularly to such an agglomerate wherein the liquid contains unidentified growth factors which are used as animal feed supplements.

2. Brief Description of the Prior Art:

The National Research Council has long recognized the existence of unidentifed growth facts (UGF) and in 1960 concluded that marine products, such as condensed fish solubles (CFS) are a major source of UGF. The accumulated evidence leaves no doubt that UGF exists and are of primary importance in promoting growth, reproduction and enhanced storage and utilization of certain vitamins and minerals. Attempts to fractionate, or concentrate, the UGF have been largely unsuccessful and of little economic importance to the animal feed manufacturer. Condensed fish solubles (CFS) in their natural state have been widely acknowledged as one of the most potent sources of UGF available. It has been the goal of scientists to develop a method of converting the CFS to a more convenient dry form and yet retain the original high UGF potency of the liquid solubles.

In the past, attempts have been made to mix these solubles with carrier material such as soy bean hulls because they are inexpensive and adsorptive. Similar organic materials have been used for the same purpose. An example is soy bean meal, which includes the carrier properties of the hulls in addition to a protein element. Dried, ground corncobs have also been used as carrier materials.

Although these materials convert the liquid CFS to a more convenient semi-dry form, it has been found that the adsorbing limitations of these organic materials require utilization of great quantities of carrier material, with respect to the CFS, which increases shipping and handling costs as well as decreases the UGF potency per unit weight. Additional problems of bacteria and mold growth have made it impractical to use the semi-dry material on a widespread basis.

Another prior art approach has been to remove the water content from the CFS in an attempt to obtain the UGF as a powdered concentrate. However, scientists have discovered that by removing the water, the UGF are destroyed. Thus, it is a basic presumption that UGF require moisture in order for the factors to remain stable.

Dr. Ed Nabor, of Ohio State University, conducted tests to demonstrate the destruction of UGF stability when heat is applied to and/or water removed from CFS. In his experimentation Dr. Nabor used heat to dry CFS under the gentlest of conditions, namely a vacuum environment. By reducing the water content of the CFS, a growth assay did not show a corresponding increase in UGF potency on a unit weight basis. Thus, it is apparent that heat and/or the drying process affects the potency or stability of the factors. Similar experiments have been carried out with other UGF sources by Dr. Larry Potter of Virginia Polytechnic Institute, Cornell University, Washington State University and other institutions which have reported the same observations.

Although the foregoing discussion related to UGF in condensed fish solubles, it must be clearly understood that UGF exists in many other organic materials. Thus, the animal feed industry utilizes liquid streptomyces solubles, a by-product from antibiotic production, as a source of UGF. Other sources include distillers' solubles, brewers' yeasts, other yeasts, molds, whey and fermented whey. These sources are utilized because they are plentiful and inexpensive. However, it must be understood that other natural materials, fermentation residues, organic substances and various combinations thereof can furnish the requisite UGF.

BRIEF DESCRIPTION OF THE INVENTION

The present invention has achieved the development of a method for converting UGF liquids, such as condensed fish solubles (CFS), liquid streptomyces solubles (LSS) and/or liquid penicillin solubles to a more convenient semi-dry form and yet retain the original high UGF potency of the liquid solubles. This is accomplished by forming an agglomerate consisting of primary and secondary carriers that adsorb the liquid soluble to their surfaces and yet form a granular composition that is extremely convenient to handle.

The particular types of carriers employed in the present invention are far superior than the prior art carriers, in terms of their adsorptive capacity. Accordingly, per unit weight, the granular composition of agglomerates that form the present invention have a high UGF yield. Because of a novel pre-treatment of the solubles, the present invention eliminates the problems of bacterial and mold growth that plagued the products conceived in the prior art.

As a result of the present agglomerate structure and its ralated method, solubles may be converted to a substantially dry, stable meal, which retains the original high UGF potency present in the natural solubles or aforementioned materials. The result of this development enables a lower feed cost with equal, or greater nutritional value of the animal ration.

It must be emphasized that although the present invention will be described in terms of its utilization for animal feed supplements (UGF), the basic method and resulting agglomerate structure can be employed in other industrial applications where a liquid is to be converted to a substantially dry form that is convenient to handle.

In certain instances, the use of the primary carrier, alone, may be adequate.

The above-mentioned objects and advantages of the present invention will be more clearly understood when considered in conjunction with the accompanying drawings, in which:

PREFERRED EMBODIMENT OF THE INVENTION

Figure 1:
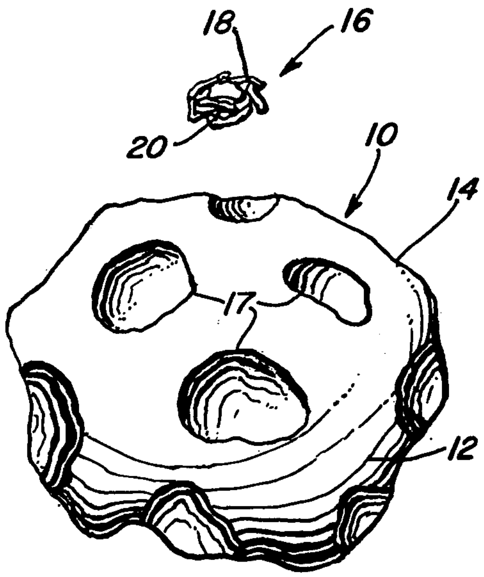
FIG. 1 is a view illustrating the primary and secondary carrier particles depicting their external appearance and relative size.

Referring to the figures, and more particularly FIG. 1, reference numeral 10 generally indicates a primary carrier particle that may consist of silicon dioxide. This material is available from the Huber Corporation of Maryland. Other carriers may also be employed. These include the generic material bentonite and the many types and forms of standard diatomaceous earths such as Celite and other inorganic oxides. Another excellent carrier material is known as Vermiculite. The qualities that these primary carrier particles have include: excellent adsorptive capability, and resistance to shearing effects due to material handling. As will be noticed from FIG. 1 the mass 12 of the carrier particle 10 has a generally spherical to cuboidal shape with an irregular surface 14 that includes craters or pockets 17 that hold significant quantities of liquid therein. This gives the primary carrier material its adsorptive quality.

Reference numeral 16 generally denotes a particle of the secondary carrier which is an expanded diatomaceous particle. The material is available from the Johns-Manville Company and is known in the trade as MICRO-CEL. The material is a diatomaceous finely ground earth of extremely small particle size which is fused with calcium oxide at high temperatures to form an expanded particle system. The resulting particle is a calcium silicate salt, which has a greatly increased surface area per unit weight when compared to the original diatomaceous earth. As will be noticed from FIG. 1, the secondary particle has many three-dimensional flanges or convolutions. Due to these flanges, the secondary particle has an extremely high adsorptive capability. This capability even exceeds that of the primary carrier. However, it is not practical to use only the secondary carrier material because the flange configuration thereof makes the secondary carrier particles extremely fragile and susceptible to shearing in the course of material handling.

Figure 2:
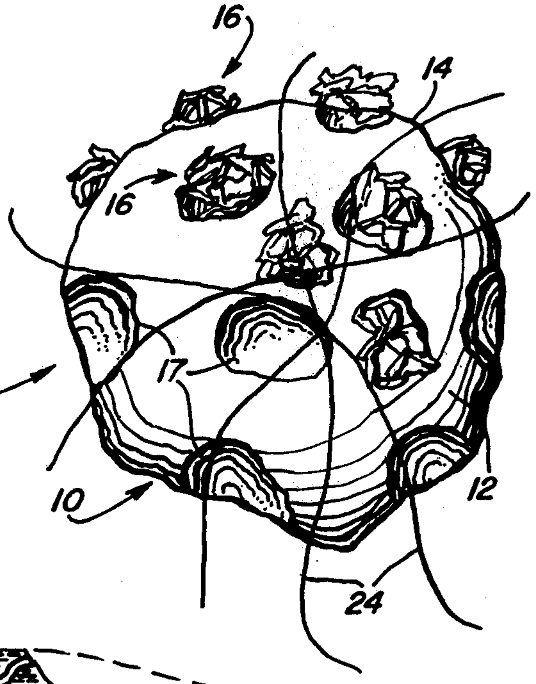
FIG. 2 is a view illustrating the composite of the carrier particles forming an agglomerate with liquid soluble absorbed by the surface of the particles.

FIG. 2 illustrates the adherence of many secondary carrier particles 16 to a single primary carrier particle 10. Although some of the secondary carrier particles may not continually adhere to the primary carrier particles, the result is an agglomeration that is fairly resistant to material handling shearing. In addition, the agglomerate carries a substantial proportion of its weight in the liquid solubles.

It has been found that the addition of cellulose fibers 24 to the agglomerate of FIG. 2 further increases the structural integrity and flowability of the resulting granular composition and significantly reduces compaction, particularly in bulk handling. The cellulose fibers may be derived from various sources including ground corncob or ground peanut hulls. The exact process for producing the agglomerate of FIG. 2 will be explained hereinafter.

PROCESS FOR MAKING AGGLOMERATE

With the preceding discussion regarding the physical structure of the agglomerate 22, it will be well to continue at this point with a discussion of how the agglomerate is formed. The basic process steps for the present invention includes:

1. pretreatment of an active liquid to retard mold and bacterial growth;
2. mixing of primary carrier and active liquid; and
3. further mixing with a secondary carrier to form a complete agglomerate structure.

The active ingredient which contains UGF may be of several conventional types. The previously mentioned condensed fish solubles provide one such active ingredient. The condensed fish soluble (CFS) are usually made from salt water fish, such as the Menhaden fish. CFS is available as a commodity from many processors such as the Hanie Products Company of Virginia and the Empire Menhagen Company of Louisiana. The Menhaden fish is prevalent along the East Coast and the Gulf of Mexico. In other coastal areas, other types of fish can be economically used. A second type of active ingredient is liquid streptomyces solubles (LSS), which is available as a by-product of the antibiotic industry. Another name for this active ingredient is streptomyces fermentation residues. A number of pharmaceutical companies offer this or similar materials as a commodity, such as Abbott Laboratories. Combinations of active ingredients may also be used, such as the combination of CFS and LSS. Also, there are a wide variety of active liquid ingredients that can be used in lieu of the ones presently enumerated such as penicillin solubles. CFS and LSS are mentioned as being exemplary.

As mentioned in the brief descriptions of the prior art and the present invention, it is an extremely important object of the invention to pre-treat the active liquid ingredients so that they retard mold growth and bacterial growth. With respect to mold growth, it has been found that the addition of acid to the active liquid decreases its pH and will create a hostile medium for molds. This is due to the fact that most molds grow readily in a neutral pH environment (pH of about 7±2). Certain molds will grow in a slightly acid material with a pH in the vacinity of 6. However, mold growth will virtually retard when the pH ranges between 1.0 and 3.0.

A preferred acid is sulfuric acid which will not only provide the necessary acidic pH, but also provides an additional nutritional benefit. The sulphate ion in sulfuric acid is a source of sulfur which has been reported to reduce an animal's requirement of methionine as derived from exogenous sources. However, it must be plainly understood that other conventional acids will provide the same mold retardant effect. although these acids may not provide the nutritional advantage of sulfuric acid due to the lack of a sulphate ion. Alternative acids are hydrochloric, nitric and phosphoric.

A second phase of active liquid pre-treatment concerns a conditioning of the liquid to raise its osmotic pressure capability thereby creating a hostile environment for bacteria, which results in bacteria-static action. Economically, sodium chloride provides satisfactory ionic action to raise the osmotic pressure to a necessary level, hostile to bacteria. Alternatives to sodium chloride are any economically available inorganic salt that may provide ions necessary to raise the osmotic pressure of the active liquid.

The sodium chloride must be added to the active liquid while the latter is maintained at an elevated temperature sufficient to completely dissolve (dissociate) the sodium and chloride ions in the liquid to achieve a saline solution in the approximate range of 2% – 6% (by weight) which is reduced (by weight) in the finished product. If the salt were not completely dissolved (dissociated or ionized), crystals would form, out of solution, and the osmotic pressure would not be increased uniformly throughout the liquid, as required.

Once the active liquid has been pre-treated to retard bacteria and mold growth, the liquid may be mixed with primary and secondary carrier material, both insoluble to the active liquid, to form the agglomerate structure shown in FIG. 2. As an initial step, the active liquid is mixed with the primary carrier, such as the silicon dioxide, previously mentioned, or other oxides. The mixing may occur in either a batch or continuous operation. Emperically, the mixing takes place for a long enough period to achieve homogenity of the mixture. However, the period of mixing must be limited because excessive mixing will denature the protein molecules of the active liquid, as well as causing structural damage to the primary carrier particles. In addition, excessive mixing or agitation will destroy the fragile UGF. Before the end of a mixing operation, cellulose fibers are introduced to the mixture so that they entwine the primary carriers. This is shown in FIG. 2. Although a substantial degree of adsorption has taken place between the primary carrier and the active liquid, the primary carrier material is saturated and as a result, excess liquid exists. Thus, the resultant mixture is damp and is not freeflowing. To rectify this condition, a second mixing step takes place which adds the secondary carrier. As in the instance of the first mixing step, the period of mixing is determined emperically so that mixing takes place for a long enough period of time to achieve homogenity of the mixture without causing denaturing of protein molecules in the active liquid, nor damage to primary carrier particles. In addition, the mixing cannot be excessive since the UGF would be destroyed by the excessive introduction of mechanical energy. Still further, the mixing period is critical due to the fragility of the secondary carrier particle flanges. Thus, if the second mixing step is too lengthy, the necessary flanges, as shown in FIG. 1, would be sheared off and the adsorption capability of the secondary carrier material would be greatly reduced. The protein denaturation and particle damage results in a thick, gumlike material which is no longer freeflowing. As a result of the second mixing step, the previously existing excessive liquid is adsorbed by the secondary carrier particles, these secondary carrier particles remaining unsaturated with the active liquid. The resulting material is granular in nature and quite freeflowing. Due to the presence of the adsorbed liquid, the granular material will not be dusty, which is a great advantage during material handling.

Figure 3:
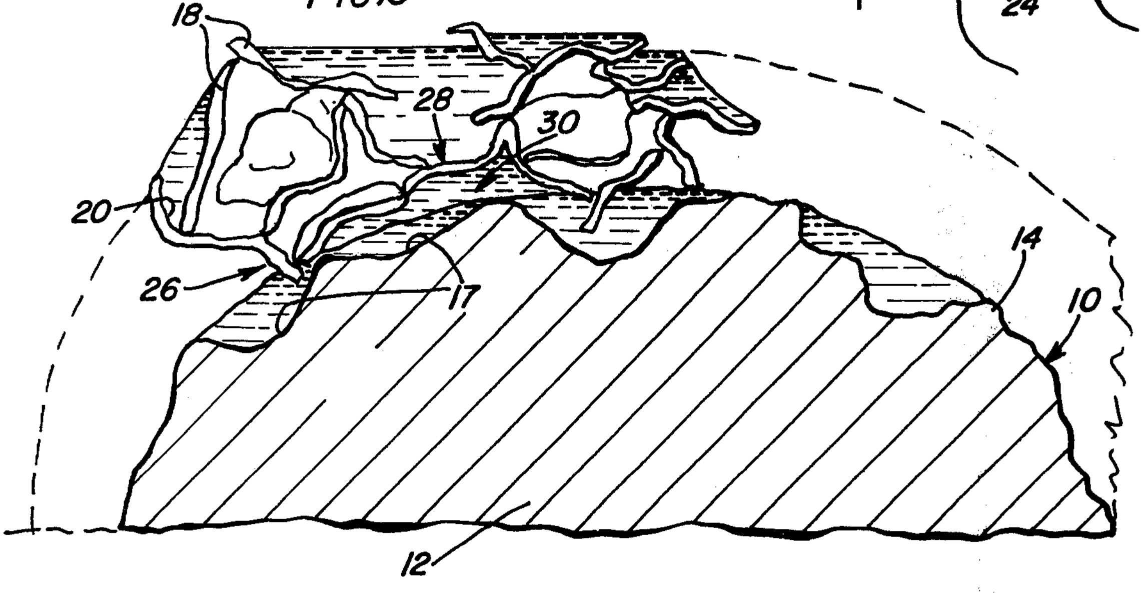
FIG. 3 is an enlarged portion of the agglomerate shown in FIG. 2. The figure illustrates the adherence of the secondary carrier particles to the primary carrier particle, with liquid being adsorbed along the exposed surfaces.

The resultant granular material is comprised of agglomerates, as shown in FIG. 2. FIG. 3 is a partial view of an agglomerate showing the structural relationship between several secondary carrier particles and a primary carrier particle. As will be noted from FIG. 3, the secondary carrier particles 16 adhere to the surface 14 of the primary particle 10, at points such as 26. Adhesion takes place due to the adhesive quality of the liquid adsorbed on the surfaces of both the primary carrier particle and the secondary carrier particles. The presence of the active liquid along the surface areas of the carrier particles is clearly evident in FIG. 3. This accounts for physical bonding of water to the carriers. In addition to this physical bonding, water is chemically bound to the carriers through the vehicle of crystals (not shown) that exist within the adsorbed liquid on the surfaces of the particles. These crystals result from a chemical reaction that occurs during the second mixing step discussed above. During this step, calcium oxide from the secondary carrier material reacts with water in the active liquid to produce calcium hydroxide, a crystal material. Accordingly, the presence of water to maintain the integrity of UGF is insured in the final agglomerate.

FIG. 3 indicates a point 28 where adjacent flanges of respective secondary carrier particles may attach due to the adhesion therebetween. Again, this is due to the adhesive quality of the active liquid. The extended flanges of the secondary carrier particles create pockets 30, between the secondary carrier particles and the peripheral surface 14 of the primary carrier particle. The pocket serves as a minute reservoir for the active liquid. In addition, FIG. 3 depicts the depressions 17 in the primary carrier which also serves as a minute reservoir for the active liquid. The previously metioned pocket 20 formed as a result of the convolutions of the flanges 18 store portions of the active liquid therein. Thus, as evidenced by FIG. 3, adjacently situated particles form liquid filled cavities for storing the active liquid. More particularly, the cavities are formed between adjacently positioned flanges 18 of the secondary particles, as well as between adjacently positioned secondary particles, primary-secondary particles, and as would be inherent in the invention, where voids are created, between adjacently situated primary particles. The resultant liquid storage capability of the agglomerate via adsorption and capillary action results in a 35% composition, by weight, of water in the finished product. This relatively high percentage of water in the finished product enables the present invention to maintain the integrity, stability and potency of UGF factors in a converted material that is dry-like, granular and convenient to handle.

The preferred embodiment of the present invention has been described above in terms of an active liquid having high nutritional value, particularly in its high UGF composition. However, it must be emphasized other liquids may be converted to a granular state using the principles of the present invention. These may include other nutritional liquids, oils, fats and fatty acids as well as a wide variety of industrial liquids, to name a few.

It is also to be emphasized that although the preceding is discussed in terms of a nutritional supplement for animals, it should be understood that the invention has application for human consumption of liquids that might contain unidentified growth factors, medicine, other nutritional liquids, or the like. Accordingly, the preceding specification must be read in that light and in the following claims, the term animal must be broadly construed to consider human as well as other high order animals.

It should be understood that the invention is not limited to the exact details of construction shown and described herein for obvious modifications will occur to persons skilled in the art.

Wherefore the following is claimed:

1. A method for converting a liquid source of unidentified growth factors to a semi-dry stable meal, which retains the original unidentified growth factors potency found in the liquid, the method including the steps:

pretreating the liquid with sulfuric acid thus decreasing the pH of the liquid and establishing a sufficiently acidic environment to retard mold growth in the meal, the sulfuric acid contributing sulphate ions to the liquid thus becoming a source of sulfur to predetermined animals that are capable of utilizing the resulting sulfur to decrease their requirements for methionine from exogenous sources;

subjecting the liquid to further pretreating with an inorganic salt providing ions in the liquid which raise the osmotic pressure thereof and creates a hostile environment which arrests bacteria growth in the meal;

combining adsorptive primary carrier particles that are shear resistant with the liquid, and insoluble in the liquid, until saturation of the particles and excess free liquid result to form damp material;

mixing separate cellulose fibers with the liquid and primary carrier particles which results in the distribution of the fibers in the meal that renders greater flowability and inhibits compactability thereto;

mixing thereto adsorptive expanded diatomaceous earth particles as secondary particles, also insoluble in the liquid, to form agglomerates, each agglomerate comprising secondary carrier particles adhering to a primary particle, the free excess liquid being adsorbed by the secondary carrier particles to form a free flowing granular material with substantial surface moisture adsorbed by each agglomerate.

2. A method for converting a nutritional liquid to a conveniently handled dry-like granular stable meal, which retains the nutritional potency of the original liquid, the method comprising the steps of:

combining adsorptive primary carrier particles that are shear resistant with a nutritional liquid, and insoluble in the liquid, until saturation of the particles results to form a damp material;

mixing thereto, secondary adsorptive carrier particles, insoluble in the liquid and smaller than the primary carrier particles for causing the formation of agglomerates, each agglomerate comprising secondary carrier particles adhering to a primary carrier particle, adjacently positioned particles of the agglomerates creating cavities filled with the liquid, the agglomerates forming a free flowing granular material with substantial surface moisture adsorbed by each agglomerate.

3. The method recited in claim 2 together with the step of pretreating the liquid with a substance that decreases the pH of the liquid so that it becomes sufficiently acidic to retard mold growth in the granular meal.

4. The method as defined in claim 3 wherein the substance is sulfuric acid that contributes sulfate ions to the liquid thus becoming a source of sulfur to predetermined animals that are capable of utilizing the resulting sulfur to decrease their requirements for methionine from exogenous sources.

5. The method as set forth in claim 2 together with the step of pre-treating the liquid with a substance that increases the osmotic pressure of the liquid thus creating a hostile environment for bacteria which arrests bacterial growth in the granular high moisture meal.

6. The method defined in claim 5 wherein the substance is an inorganic salt providing ions in the liquid which raise the osmotic pressure thereof.

7. The method defined in claim 2 wherein the secondary carrier particles are expanded diatomaceous earth particles.

8. The method defined in claim 2 together with the step of mixing separate cellulose fibers with the liquid and the primary carrier particles resulting in the distribution of the fibers in the meal that renders greater flow capability thereto.

9. A method for converting a liquid source of unidentified growth factors to a dry-stable meal, which retain the original unidentified growth factors potency found in the liquid, the method including the steps:

combining adsorptive primary carrier particles that are shear resistant with the liquid, and insoluble in the liquid, until a saturation of the particles and excess free liquid result to form a damp material;

mixing thereto, adsorptive expanded diatomaceous earth particles, insoluble in the liquid, as secondary carrier particles, to form agglomerates, each agglomerate comprising secondary carrier particles adhering to a primary carrier particle, the free excess liquid being adsorbed by the secondary carrier particles to form a free flowing granular material with substantial surface moisture adsorbed by each agglomerate.

10. A method for converting a liquid to a semi-dry granular form that is convenient to handle, the method comprising the following steps:

combining adsorptive primary carrier particles that are resistant to shearing, with a liquid, the particles insoluble in the liquid, until saturation of the particles results to form a damp material;

mixing thereto secondary adsorptive carrier particles, insoluble in the liquid and smaller than the primary carrier particles, for causing the formation of agglomerates, each agglomerate comprising secondary carrier particles adhering to a primary carrier particle, adjacently positioned particles of the agglomerates creating cavities filled with the liquid, the agglomerates forming a free flowing granular material with substantial surface moisture adsorbed by each agglomerate.

* * * * *